United States Patent
Shanmugavel et al.

(10) Patent No.: US 6,985,556 B2
(45) Date of Patent: Jan. 10, 2006

(54) PROXIMITY DETECTOR AND RADIOGRAPHY SYSTEM

(75) Inventors: Giridharan Shanmugavel, Bangalore (IN); Hariharan Krishnaswami, Bangalore (IN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 150 days.

(21) Appl. No.: 10/639,882

(22) Filed: Aug. 13, 2003

(65) Prior Publication Data
US 2004/0125918 A1 Jul. 1, 2004

(30) Foreign Application Priority Data
Dec. 27, 2002 (JP) ............................. 2002-379671

(51) Int. Cl.
*H05G 1/54* (2006.01)

(52) U.S. Cl. ................. 378/117; 378/197; 324/678; 324/687; 250/363.02

(58) Field of Classification Search ................ 378/91, 378/114, 117, 196, 197, 205; 324/661, 662, 324/668, 663, 678, 679, 686, 687, 658; 340/540, 340/541, 561, 562; 250/363.02, 363.03, 250/363.04, 363.05, 363.08
See application file for complete search history.

(56) References Cited

U.S. PATENT DOCUMENTS

| | | | |
|---|---|---|---|
| 5,166,679 A | 11/1992 | Vranish | |
| 5,212,621 A | 5/1993 | Panter | |
| 5,363,051 A | 11/1994 | Jenstrom | |
| 5,373,245 A | 12/1994 | Vranish | |
| 5,583,909 A | 12/1996 | Hanover | |
| 5,651,044 A | 7/1997 | Klotz | |
| 5,726,581 A | 3/1998 | Vranish | |
| 5,764,145 A | 6/1998 | Hansson | |
| 5,805,658 A | 9/1998 | Hum | |
| 5,883,935 A | 3/1999 | Habraken | |
| 5,964,478 A | 10/1999 | Stanley | |
| 6,020,812 A * | 2/2000 | Thompson et al. ......... 340/438 |
| 6,079,738 A | 6/2000 | Lotito | |
| 6,260,879 B1 | 7/2001 | Stanley | |
| 6,307,384 B2 | 10/2001 | Havey | |
| 6,348,862 B1 | 2/2002 | McDonnell | |
| 6,408,051 B2 | 6/2002 | Habraken | |
| 6,430,259 B2 * | 8/2002 | Meek et al. ................ 378/117 |
| 6,445,294 B1 | 9/2002 | McDonnell | |
| 6,661,239 B1 * | 12/2003 | Ozick .......................... 324/658 |
| 2003/0132763 A1 * | 7/2003 | Ellenz ......................... 324/663 |

FOREIGN PATENT DOCUMENTS
FR 2693555 1/1994

* cited by examiner

Primary Examiner—Edward J. Glick
Assistant Examiner—Chih-Cheng Glen Kao
(74) Attorney, Agent, or Firm—McAndrews, Held & Malloy, Ltd.; Peter J. Vogel; Michael A. Dellapenna

(57) ABSTRACT

Certain embodiments of the present invention provide a proximity detector having a simple configuration and an imaging system including the proximity detector. In an embodiment, a proximity detector mainly comprises: a single electrode mounted on a subject-side end of a movable member; a current feeding device for feeding a constant current to an electrostatic capacitor formed between the electrode and a ground; a discharging device for releasing charge from the electrostatic capacitor at intervals of a certain cycle; a binary-coding device for binary-coding the potential at the electrode relative to a ground based on a threshold; and a smoothing device for smoothing an output signal of the binary-coding device.

20 Claims, 6 Drawing Sheets

Mathematical 1

$$v = \frac{1}{C} \int I \, dt$$

PROXIMITY DETECTOR AND RADIOGRAPHY SYSTEM

RELATED APPLICATIONS

The present application claims priority under 35 U.S.C. 119 to Japanese Patent Application No. JP2002-379671, filed on Dec. 27, 2002, to Giridharan Shanmugavel and Hariharan Krishnaswami.

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention relates to a proximity detector and a radiography system, and more particularly, to a proximity detector for detecting the proximity of a movable unit to a subject using proximity sensing and to a radiography system including the proximity detector.

Imaging systems, such as x-ray radiography systems, are typically positioned close to a patient or subject to be imaged in order to provide desired imaging information. One type of radiation imager is a mobile C-arm system. In the medical field, the mobile C-arm system may be used for general surgery, orthopedic procedures, pain management procedures, vascular procedures, and cardiac procedures, for example. Typically, the mobile C-arm has an x-ray source mounted at one end of a mainframe and a detector, such as an image intensifier, mounted at the other end of the mainframe. The mobile C-arm may be moved in relation to the object, such as a patient, to be imaged.

Motorized motion of any of the axes of a mobile C-arm system poses possible risks to the patient and to the imaging system and other equipment. It is desirable to prevent or minimize collisions between the mobile C-arm and the object. A possibility of collision exists whether the C-arm is moved through automated trajectory tracking or through direct user input from a user interface device. It is therefore desirable to prevent or minimize collisions when the mobile C-arm is controlled by both an external user and by an automated system. A method and system for preventing collision between a mobile C-arm and an object would be highly desirable.

Imaging systems typically use one of two types of anti-collision sensors: contact sensors and proximity sensors. A contact sensor may use a bumper. The contact sensor detects a change in pressure resulting when the bumper contacts the object.

A proximity sensor detects the presence of an object within a given distance from a movable part of the C-arm imaging apparatus. A proximity sensor may be a capacitive proximity sensor. Typically, a plurality of capacitive sensor plates are used. A multiplexor selectively electrically couples the sensor plates and a capacitive sensing processing unit. Conventional sensor systems may also incorporate shielding to prevent detection of components in the imaging apparatus.

Proximity detection may be enhanced using two additional electrodes. One electrode may be used as a receiver. The other electrode is used as a transmitter and attached to the face of the x-ray detector, such as an image intensifier. Proximity detection with the two electrodes is based on a radio frequency (RF) coupling between the transmitting and receiving electrodes.

Current proximity sensor systems use several sensor plates. The sensor plates are placed around the x-ray detector (e.g., image intensifier) and in the face of the detector. Scanning circuitry includes a multiplexor to accommodate the plurality of sensor plates. The scanning circuitry increases overhead on sensing circuitry for the imaging system. U.S. Pat. No. 5,651,044, to Klotz et al., relates to one such multi-plate proximity sensor system.

Additionally, proximity sending is currently performed using RF coupling with both a transmitter and receiver. Capacitance is detected by a change in an electromagnetic field created by the transmitter when an object passes near the transmitter.

Current proximity sensors are limited by the complexity of electronic circuitry. Complex, additional electrical circuitry impacts the cost, maintenance, and performance, for example, of the imaging system. Current sensor systems are also limited by distances between sensors and imaging system components. That is, operating constraints limit the distance between a proximity sensor and an image intensifier, for example. Additionally, current sensor systems are limited by the use of an electromagnetic field for proximity detection. Furthermore, capacitive proximity sensing has not been used with a mobile C-arm apparatus.

Thus, a need exists for an improved proximity sensing mechanism using capacitive sensing techniques on a mobile C-arm apparatus.

BRIEF SUMMARY OF THE INVENTION

Certain embodiments of the present invention provide a proximity detector having a simple configuration and an imaging system including the proximity detector. In a certain embodiment, the imaging system includes a movable member capable of approaching a subject and a proximity detector. The proximity detector indicates an approach of the movable member within a certain distance of the subject based on an electric field. The proximity detector includes an electrode mounted on the movable member, a current feeding device for feeding a current to an electrostatic capacitor formed between the electrode and a ground, and a discharging device for releasing charge from the electrostatic capacitor at intervals of certain cycle.

The proximity detector may also include a binary-coding device for binary-coding a potential at the electrode relative to a ground based on a threshold and a smoothing device for smoothing an output signal of the binary-coding device. The electrode may include two conductive layers electrically isolated from each other. The current may be fed to an outer layer of the conductive layers. Identical voltages may be applied to the outer and inner layers. The imaging system may also include an x-ray irradiating device and an x-ray receiving device supported by the movable member. The x-ray irradiating device and x-ray receiving device may be positioned opposed to each other with a space therebetween. The x-ray receiving device may include in image intensifier. The movable member may be a C-arm. The electrode may be formed along a perimeter of a receiving surface of the x-ray receiving device. The electrode may also be formed over an outer periphery of the x-ray receiving device and a perimeter of a receiving surface thereof.

In a certain embodiment, the proximity detector includes an electrode positioned on a surface, a current feeding device for feeding a current to an electrostatic capacitor formed between the electrode and a ground, a discharging device for releasing charge from the electrostatic capacitor at intervals of a certain cycle, and a proximity detection triggering an alert based on a threshold. The alert may be an alarm, a report, and/or a command, such as a motion halt command. In an embodiment, the current fed to the electrostatic capacitor may be a constant current.

The proximity detector may also include a binary-coding device for binary-coding a potential at the electrode relative to a ground based on a threshold, and a smoothing device for smoothing an output signal of the binary-coding device. The electrode may include two conductive layers electrically isolated from each other. The current may be fed to an outer layer of the conductive layers, and a voltage may be applied to the outer and inner layers. In an embodiment, the proximity detector uses a ramp and pedestal method to detect a change in capacitance.

In an embodiment, the proximity detector may be used with an x-ray irradiating device and an x-ray receiving device supported by a supporting device. The x-ray irradiating device and x-ray receiving device may be positioned opposed to each other with a space therebetween. The electrode may be formed along a perimeter of a receiving surface of the x-ray receiving device. The electrode may also be formed over an outer periphery of the x-ray receiving device and a perimeter of a receiving surface thereof.

In a certain embodiment, the method for proximity detection includes positioning an electrode on a surface, forming an electrostatic capacitor between the electrode and a ground, feeding a current to the electrostatic capacitor, releasing a charge from the electrostatic capacitor at certain intervals, comparing a voltage across the electrode to a reference signal to form a proximity detection signal, and triggering an alert if the proximity detection signal does not satisfy a certain threshold. The method may also include generating a binary signal based on the voltage and the reference signal, and smoothing the binary signal to form a proximity detection signal. Additionally, the method may include positioning a patient and triggering an alert when the surface approaches the patient within a certain threshold distance based on the proximity detection signal.

In an embodiment, since the single electrode is adopted, the configuration of a sensor is simplified. Moreover, a constant current is fed to the electrostatic capacitor formed between the electrode and a ground. Charge is released from the electrostatic capacitor at intervals of a certain cycle. A potential at the electrode relative to a ground is binary coded based on a threshold. An output signal of the binary-coding device is smoothed in order to produce a detection signal. This results in the simplified configuration of an electric circuit.

In an embodiment, the electrode has two conductive layers electrically isolated from each other. The constant current is fed to an outer layer of the conductive layers, and a voltage same as one applied to the outer layer is applied to an inner layer. In this case, sensitivity to be attained in proximity detection improves.

In an embodiment, the electrode is formed along a perimeter of a receiving surface of the x-ray receiving device, so that the adverse effect on incident x-rays may be minimized. In an embodiment, the electrode is formed over a periphery of the x-ray receiving device and a perimeter of a receiving surface thereof. In this case, while the adverse effect on incident x-rays may be minimized, the area of the electrode may be increased.

In an embodiment, the supporting device supports the x-ray irradiating device and x-ray receiving device at respective ends of a C-arm. In this case, diverse accesses to a subject are permitted. In an embodiment, the x-ray receiving device includes image intensifier so that the sensitivity to incident x-rays may be improved.

Certain embodiments of the present invention provide a proximity detector having a simple configuration and an imaging system including the proximity detector.

DETAILED DESCRIPTION OF THE INVENTION

For the purposes of illustration only, the following detailed description references a certain embodiment of an x-ray radiography system using a C-arm. It is understood that the present invention may be used with other imaging systems, such as a mobile C-arm system or other imaging modality.

Figure 1:
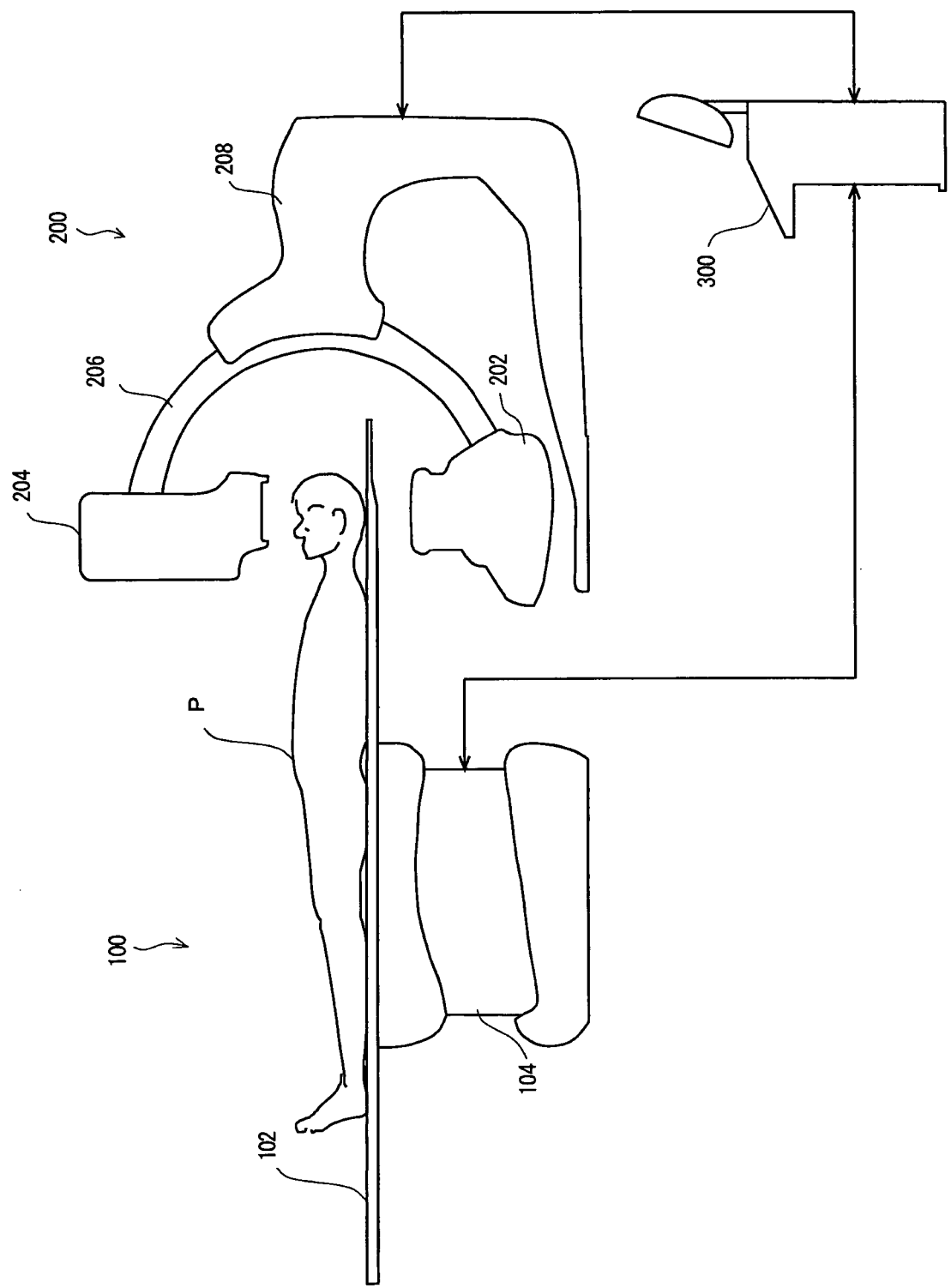
FIG. 1 illustrates a configuration of a radiography system used in accordance with an embodiment of the present invention.

FIG. 1 illustrates a configuration of a radiography system used in accordance with an embodiment of the present invention. The radiography system includes a table 100, a gantry 200, and an operator console 300.

The table 100 has a tabletop 102. A subject P of radiography is positioned on the tabletop 102. The tabletop 102 is supported by a base 104. An advancing/withdrawing mechanism, a raising/lowering mechanism, and a tilting mechanism are incorporated in the base 104. The mechanisms advance, withdraw, raise, lower, and/or tilt the tabletop 102.

The gantry 200 includes an arc-shaped C-arm 206 for supporting an x-ray irradiator 202 and an x-ray receiver 204. The irradiator 202 and receiver 204 are located opposed to each other. The arm 206 is supported by a stand 208.

The x-ray irradiator 202 has a built-in x-ray tube and irradiates x-rays towards the x-ray receiver 204. The x-ray receiver 204 has a built-in image intensifier and receives the x-rays irradiated from the x-ray irradiator 202. The x-ray receiver 204 is, for example, generally, shaped like a cylinder.

The x-ray irradiator 202 is an example of an embodiment of an x-ray irradiating device included in the present invention. The x-ray receiver 204 is an example of an embodiment of an x-ray receiving device included in the present invention, and is also an example of an embodiment of a movable member included in the present invention. The arm 206 is an example of an embodiment of a supporting device included in the present invention.

The support structure or gantry 200 has an isocenter in an interspace between the x-ray irradiator 202 and x-ray receiver 204. The isocenter is equivalent to a center of an arc of the arm 206.

A feeding or positioning mechanism incorporated in the stand 208 moves the arm 206 along an arc, for example, whereby the x-ray irradiator 202 and x-ray receiver 204 rotate with the isocenter as a center while maintaining the opposed relationship. Using the advancing/withdrawing mechanism incorporated in the arm 206, the x-ray receiver 204 may be advanced or withdrawn in the direction of the isocenter. A degree of advancing, withdrawing, raising, lowering, and/or tilting the tabletop 102 may be adjusted so that a radiographic center of the subject P will coincide with the isocenter.

The operator console 300 serves as a user interface, such as a mechanical interface, computer interface, joystick, or other interface. The operator console 300 may include information processing equipment, for example, a computer and peripheral equipment. The operator console 300 controls the table 100 and gantry 200 in response to a user-entered command. The operator console 300 may also facilitate radiography or other imaging or processing.

Figure 2:
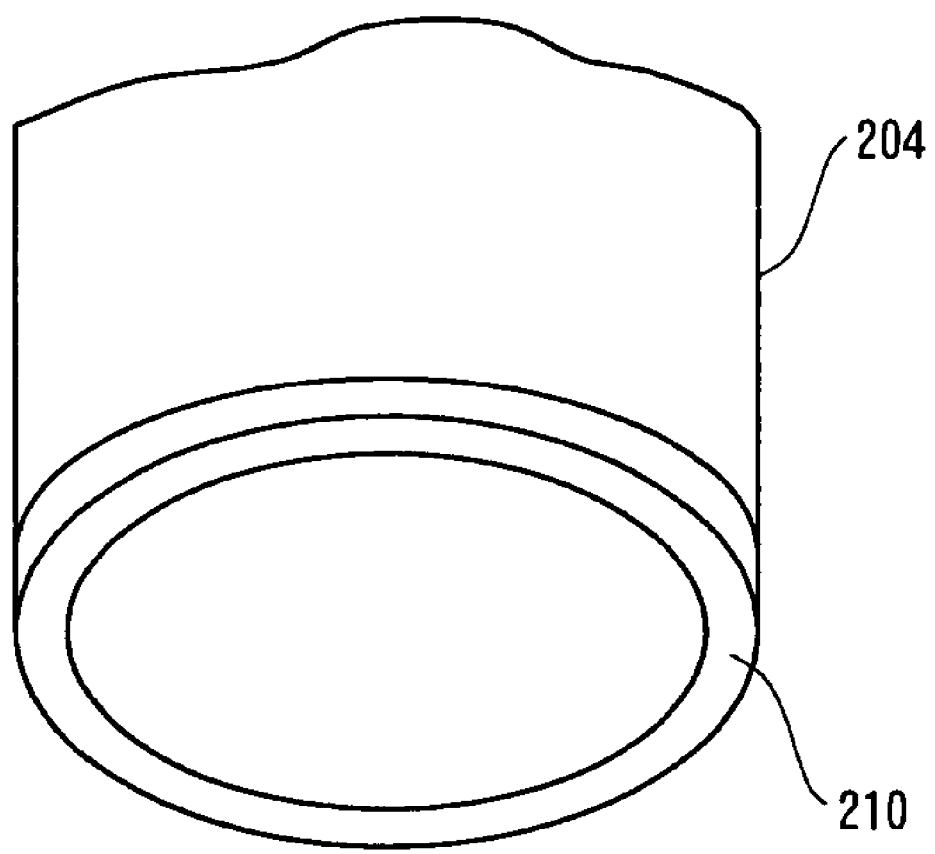
FIG. 2 illustrates an electrode used in a proximity detector in accordance with an embodiment of the present invention.

In an embodiment, the radiography system includes a proximity detector. An embodiment of the proximity detector will be described below. FIG. 2 illustrates an electrode used in a proximity detector in accordance with an embodiment of the present invention. As shown in FIG. 2, an electrode 210 is mounted on one end of the x-ray receiver 204. In an embodiment, the end of the x-ray receiver 204 is an end on the side facing the subject P, that is, on the receiving surface-side.

In an embodiment, the electrode 210 is formed over a perimeter of a receiving surface of the x-ray receiver 204 and a periphery of an end of the x-ray receiver 204. In an embodiment, the receiving surface of the x-ray receiver 204 and the peripheral surface of the end thereof are covered with an enclosure made of an insulating material, for example, a plastic. The electrode 210 may also be covered with an enclosure made of an insulating material (not shown).

Figure 3:
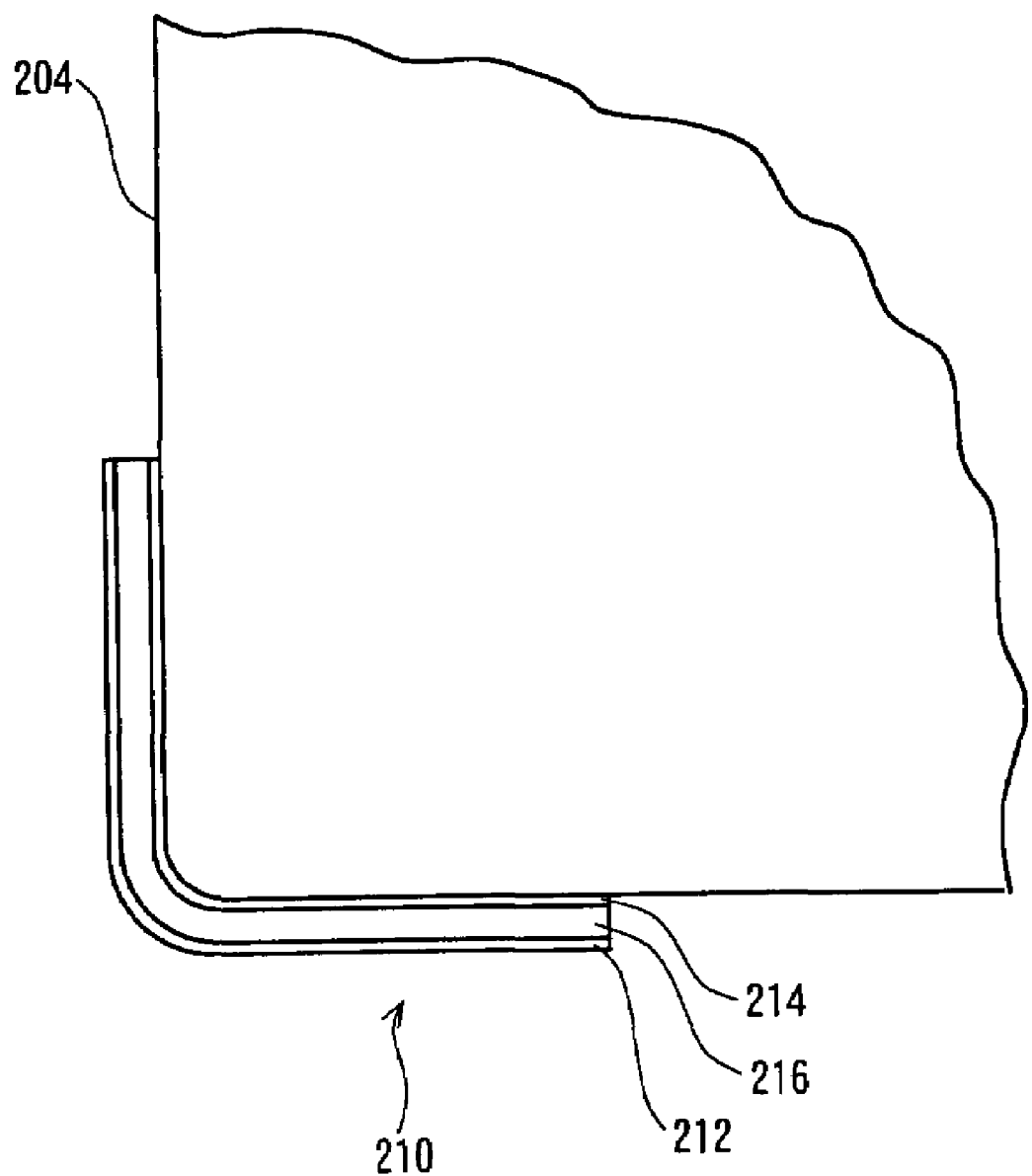
FIG. 3 illustrates an enlarged sectional view of a portion of the x-ray receiver including the electrode used in accordance with an embodiment of the present invention.

FIG. 3 illustrates an enlarged sectional view of a portion of the x-ray receiver including the electrode 210 used in accordance with an embodiment of the present invention. As shown in FIG. 3, the electrode 210 has two conductive layers 212 and 214. The conductive layers 212 and 214 are stacked up with an insulating layer 216 between them. The conductive layers 212 and 214 are layers of conductors made of, for example, copper or aluminum. The electrode 210 may be formed using, for example, a flexible printed-circuit board.

In an embodiment, the electrode 210 is formed as a single electrode. The electrode 210 is composed of a portion mounted on the receiving surface of the x-ray receiver 204 and a portion mounted on the peripheral surface of the end of the x-ray receiver 204. After the portions are mounted on the x-ray receiver 204, the corresponding conductive layers included in the portions may be electrically coupled to each other. This also results in an electrically single electrode. Alternatively, the electrode 210 may be mounted on the receiving surface of the x-ray receiver 204.

Figure 4:
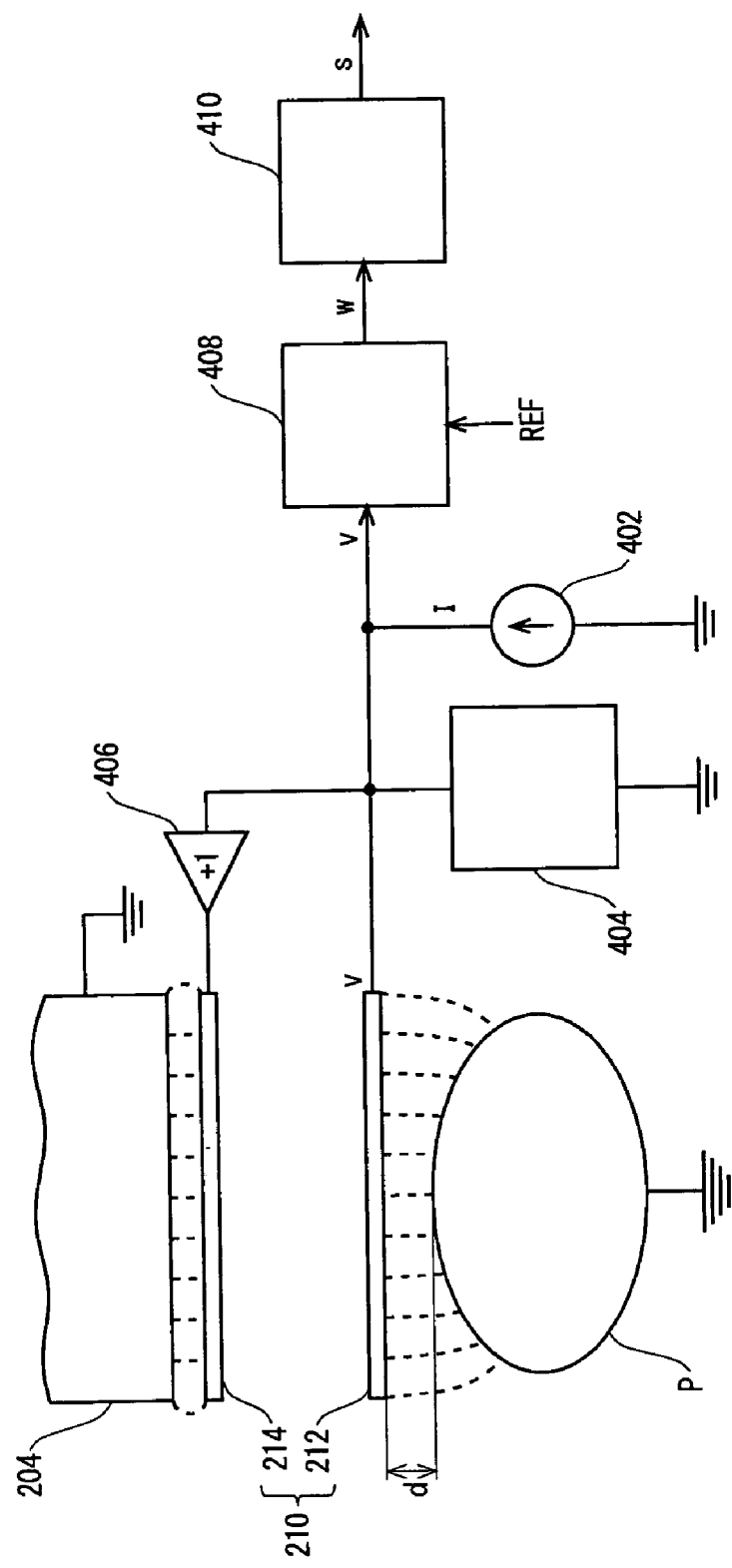
FIG. 4 shows a block diagram of a proximity detector used in accordance with an embodiment of the present invention.

FIG. 4 shows a block diagram of a proximity detector used in accordance with an embodiment of the present invention. As shown in FIG. 4, the electrode 210 serves as one electrode of an electrostatic capacitor having a ground as the other electrode. Both the subject P and the x-ray receiver 204 have a ground potential. The conductive layer 212 forms a capacitor together with the subject P, while the conductive layer 214 forms a capacitor together with the x-ray receiver 204. Hereinafter, the conductive layers 212 and 214 may be called electrodes.

A constant current source 402 is connected to the electrode 212. The constant current source 402 is an example of an embodiment of a current feeding device included in the present invention. Assuming that the electrostatic capacitance of the capacitor is C, the relationship between a current I and a voltage v developed across the electrode 212 is provided as follows:

$$V = \frac{1}{C}\int I dt. \qquad (1)$$

In an embodiment, since the current I is a constant current, the voltage v increases linearly with the passage of time. The slope of the increase in the voltage is 1/C. That is, the slope is inversely proportional to the electrostatic capacitance C.

A discharging circuit 404 is connected to the electrode 212. The discharging circuit 404 is an example of an embodiment of a discharging device used in accordance with an embodiment of the present invention. The discharging circuit 404 releases charge from the capacitor formed with the electrode 212 at intervals of a certain cycle. The release of charge brings the voltage v to a zero level periodically. Due to the repetition of charging and discharging, the voltage v assumes a sawtooth wave having the certain cycle (e.g., a ramp and pedestal waveform).

In an embodiment, the slope of the sawtooth wave in one direction of progress thereof is inversely proportional to the electrostatic capacitance C. The electrostatic capacitance C increases with a decrease in the distance d between the electrode 212 and subject P. The slope of the sawtooth wave diminishes with the decrease in the distance d between the electrode 212 and subject P.

The voltage v across the electrode 212 is applied to the electrode 214 via a voltage repeater 406. The voltage repeater 406 is realized with a high-impedance amplifier that produces a gain of, for example, +1. The voltage repeater 406 produce potential at the electrode 214 equal to the potential at the electrode 212. If the potentials at the electrodes 212 and 214 are equal, no electric field is formed between the electrodes 212 and 214. Then, an electric field around the electrode 212 may be formed on the subject side of the electrode 212. The field formed on the side of the electrode 212 toward the subject P allows proximity detection to be carried out in excellent sensitivity. In an embodiment, an electric field around the electrode 214 is formed on the x-ray receiver side of the electrode 214.

The voltage v across the electrode 212 is applied to a comparing circuit 408. The comparing circuit 408 produces a binary signal w, which signifies whether an input signal is larger, using a reference signal REF. The binary signal w is smoothed by a smoothing circuit 410 and transmitted as a proximity detection signal s. The comparing circuit 408 is an example of an embodiment of a binary-coding device used in accordance with an embodiment of the present invention. The smoothing circuit 410 is an example of an embodiment of a smoothing device used in accordance with an embodiment of the present invention.

The foregoing electric circuit may be incorporated in, for example, the enclosure covering the x-ray receiver 204. The electrode 210 may be formed with a flexible printed-circuit board extended to a certain degree. The electric circuit is then formed as a printed circuit on the extension of the electrode 210. In an embodiment, the proximity detector is constructed as a unit.

Figure 5:
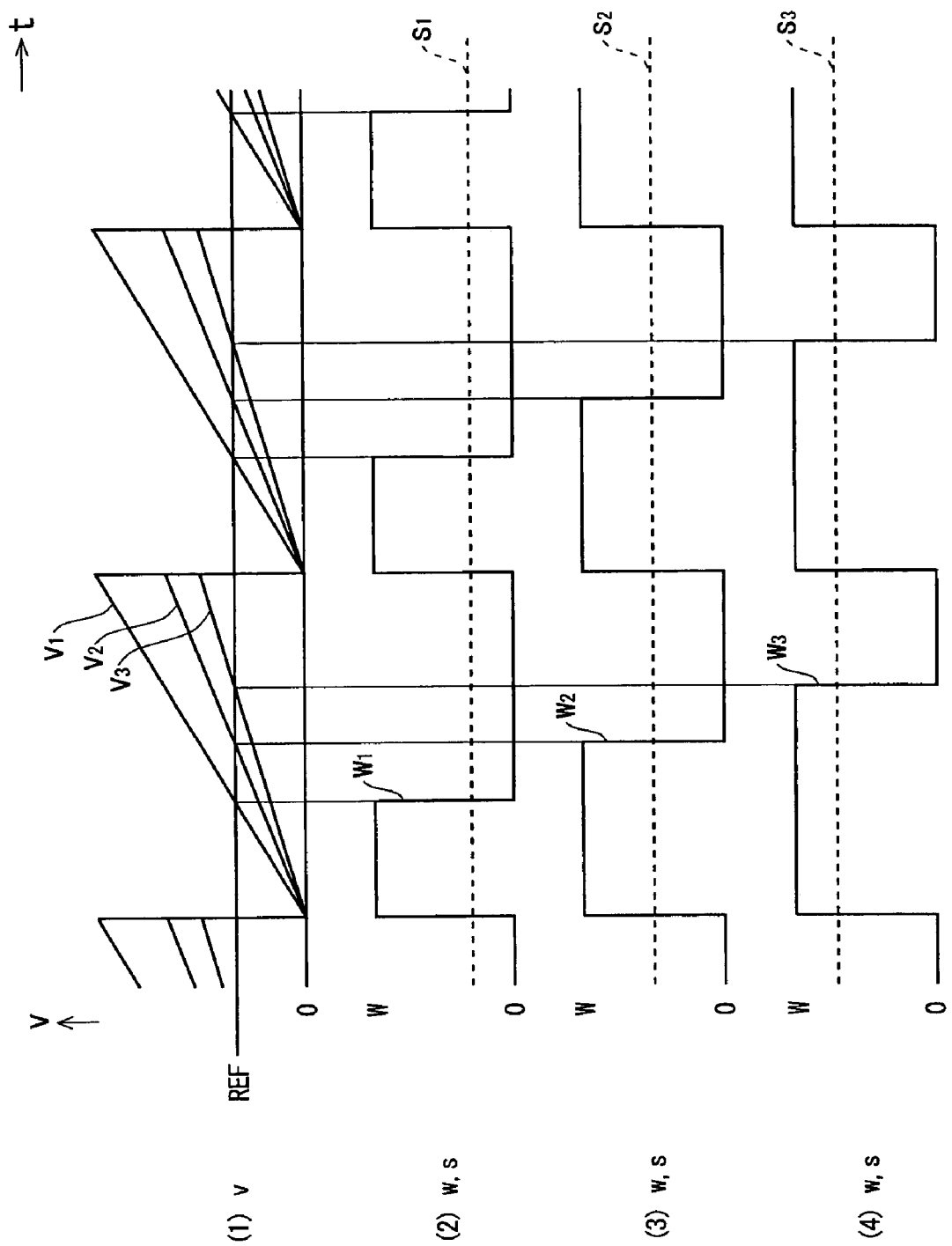
FIG. 5 illustrates a timing diagram for actions performed by the proximity detector in accordance with an embodiment of the present invention.

FIG. 5 illustrates a timing diagram for actions performed by the proximity detector in accordance with an embodiment of the present invention. Referring to FIG. 5, (1) indicates timing of the voltage v, and (2) to (4) indicate timings of the binary signal w and proximity detection signal s.

As shown in FIG. 5, the voltage v assumes a sawtooth wave having a certain cycle. The slope of the sawtooth wave in one direction of progress diminishes along with a decrease in the distance d between the electrode 212 and subject P, as indicated with, for example, oblique lines v1, v2, and v3 in FIG. 5.

Binary signals w1, w2, and w3 indicate whether respective sawtooth waves v1, v2, and v3 are larger than the reference signal REF. In an embodiment, duty ratios of the binary signals w1, w2, and w3 are in order of increasing magnitude.

In an embodiment, proximity detection signals s1, s2, and s3 result from smoothing of the respective binary signals w1, w2, and w3. In an embodiment, signal strengths of the proximity detection signals s1, s2, and s3 are in order of increasing magnitude.

Figure 6:
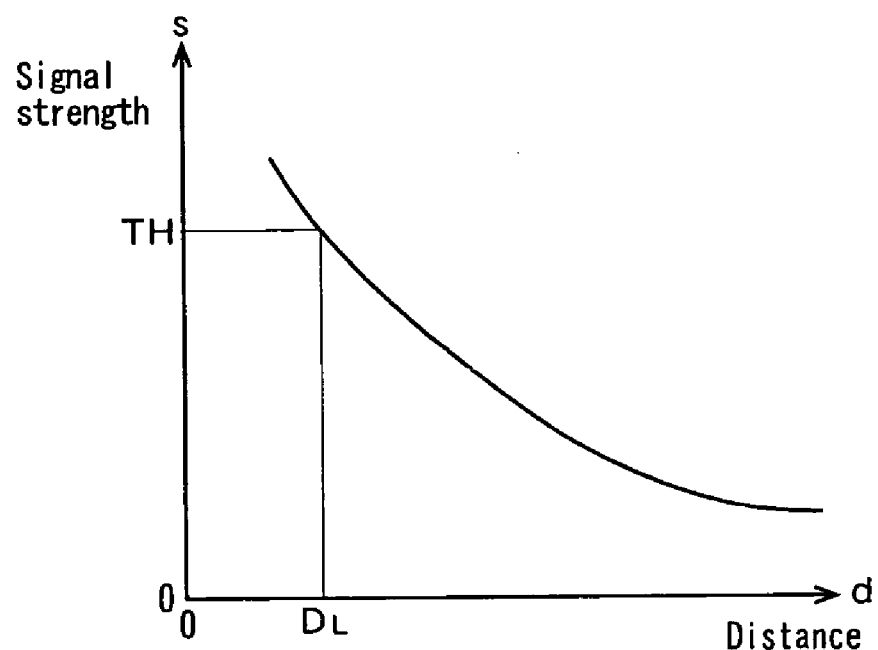
FIG. 6 depicts a relationship between a distance and a detection signal used in accordance with an embodiment of the present invention.

FIG. 6 depicts a relationship between a distance and a detection signal used in accordance with an embodiment of the present invention. A proximity detection signal s with a signal strength increasing with a decrease in the distance d may be produced. A degree of proximity of the x-ray receiver 204 to the subject P may be determined based on the signal strength of the proximity detection signal s. The proximity detection signal s may be used to trigger a proximity alarm or prevent contact of the x-ray receiver 204 or other system component with the subject P through verification based on a threshold TH corresponding to a limit DL of proximity (for example, by halting motion of the arm 206).

For example, a patient is placed on the tabletop 102 that is positioned between the x-ray receiver 204 and the x-ray irradiator 202 mounted on the C-arm 206. A gantry moves the C-arm 106. Moving the C-arm 106 positions the x-ray receiver 204 and the x-ray irradiator 202 at desired locations with respect to the patient. The x-ray receiver 204 may be positioned near the patient in order to improve resulting image quality. The proximity detector may use a ramp of peak voltage 5V and a frequency of 100 kHz. The reference voltage 250 may be set at 4V, for example. When the peak of the voltage ramp drops below the reference voltage 250, a signal is sent indicating the presence of a human body in the proximity of the capacitive proximity sensing circuit mounted on the x-ray receiver 204 or other component of the radiography system. When the proximity detector detects the presence of the patient, a motor moving the C-arm 206 may be stopped or slowed to avoid a collision with the patient.

For example, a patient is placed on the tabletop 102 that is positioned between the x-ray receiver 204 and the x-ray irradiator 202 mounted on the C-arm 206. A gantry moves the C-arm 106. Moving the C-arm 106 positions the x-ray receiver 204 and the x-ray irradiator 202 at desired locations with respect to the patient. The x-ray receiver 204 may be positioned near the patient in order to improve resulting image quality. The proximity detector may use a ramp of peak voltage 5V and a frequency of 100 kHz. The reference voltage may be set at 4V, for example. When the peak of the voltage ramp drops below the reference voltage, a signal is sent indicating the presence of a human body in the proximity of the capacitive proximity sensing circuit mounted on the x-ray receiver 204 or other component of the radiography system. When the proximity detector detects the presence of the patient, a motor moving the C-arm 206 may be stopped or slowed to avoid a collision with the patient.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. An imaging system, said imaging system comprising:
a movable member capable of approaching a subject; and
a proximity detector, said proximity detector indicating an approach of said movable member within a certain distance of said subject based on an electric field, said proximity detector comprising:
an electrode mounted on said movable member;
a current feeding device for feeding a constant current to an electrostatic capacitor formed between said electrode and a ground; and
a discharging device for releasing charge from said electrostatic capacitor at intervals of a certain cycle,
wherein said electrode comprises two conductive layers electrically isolated from each other, and said constant current is fed to an outer layer of said conductive layers, and a voltage equal to a first voltage applied to said outer layer is applied to an inner layer.

2. The system of claim 1, wherein said proximity detector further comprises:
a binary-coding device for binary-coding a potential at said electrode relative to a ground based on a threshold; and
a smoothing device for smoothing an output signal of said binary-coding device.

3. The system of claim 1, further comprising an x-ray irradiating device and an x-ray receiving device supported by said movable member, said x-ray irradiating device and said x-ray receiving device positioned opposed to each other with a space there between.

4. The system of claim 3, wherein said electrode is formed along a perimeter of a receiving surface of said x-ray receiving device.

5. The system of claim 3, wherein said electrode is formed over an outer periphery of said x-ray receiving device and a perimeter of a receiving surface thereof.

6. The system of claim 3, wherein said x-ray receiving device comprises an image intensifier.

7. The system of claim 1, wherein said movable member comprises a C-arm.

8. The system of claim 1, wherein said imaging system comprises a sensing circuit mounted on the same movable member as the electrode.

9. A proximity detector, said proximity detector comprising:
an electrode positioned on a surface of a movable member;

a current feeding device for feeding a constant current to an electrostatic capacitor formed between said electrode and a ground;

a discharging device for releasing charge from said electrostatic capacitor at intervals of a certain cycle; and a proximity detection device triggering an alert based on a threshold, wherein said electrode comprises two conductive layers electrically isolated from each other, and said constant current is fed to an outer layer of said conductive layers, and a voltage equal to a first voltage applied to said outer layer is applied to an inner layer.

10. The proximity detector of claim 9, wherein said alert comprises at least one of an alarm, a log, and a motion halt command.

11. The proximity detector of claim 9, wherein said proximity detector further comprises:

a binary-coding device for binary-coding a potential at said electrode relative to a ground based on a threshold; and a smoothing device for smoothing an output signal of said binary-coding device.

12. The proximity detector of claim 9, wherein the proximity detector is used with an x-ray irradiating device and an x-ray receiving device supported by a supporting device, said x-ray irradiating device and said x-ray receiving device positioned opposed to each other with a space therebetween.

13. The proximity detector of claim 12, wherein said electrode is formed along a perimeter of a receiving surface of said x-ray receiving device.

14. The proximity detector of claim 12, wherein said electrode is formed over an outer periphery of said x-ray receiving device and a perimeter of a receiving surface thereof.

15. The proximity detector of claim 9, wherein said proximity detector uses a ramp and pedestal method to detect a change in capacitance.

16. The proximity sensor of claim 9, wherein said proximity detector comprises a sensing circuit positioned on the same movable member as the electrode.

17. A method for proximity detection, said method comprising:

positioning an electrode on a surface of a movable member, wherein said electrode comprises two conductive layers electrically isolated from each other;

forming an electrostatic capacitor between said electrode and a ground;

feeding a constant current to said electrostatic capacitor, wherein said feeding step feeds said constant current to an outer layer of said conductive layers;

releasing a charge from said electrostatic capacitor at certain intervals;

comparing a voltage across said electrode to a reference signal to form a proximity detection signal;

triggering an alert if said proximity detection signal does not satisfy a certain threshold; and applying a voltage equal to a first voltage applied to said outer layer to an inner layer.

18. The method of claim 17, wherein said comparing step further comprises:

generating a binary signal based on said voltage and said reference signal; and smoothing said binary signal to form a proximity detection signal.

19. The method of claim 17, further comprising:

positioning a patient; and triggering an alert when said surface approaches said patient within a certain threshold distance based on said proximity detection signal.

20. The method of claim 17, wherein said positioning step further comprises positioning a sensing circuit on the same surface movable member as the electrode.

* * * * *

UNITED STATES PATENT AND TRADEMARK OFFICE
CERTIFICATE OF CORRECTION

PATENT NO. : 6,985,556 B2
DATED : January 10, 2006
INVENTOR(S) : Shanmugavel et al.

It is certified that error appears in the above-identified patent and that said Letters Patent is hereby corrected as shown below:

<u>Column 7, line 58 to Column 8, line 7,</u>
delete the complete paragraph and insert the following:
-- Thus, certain embodiments provide a capacitive proximity sensor for a mobile or fixed room C-arm imaging system. Certain embodiments of the present invention address the problems of complexity in geometry and electronic sensing circuitry in traditional capacitive proximity sensors. Capacitive proximity sensing for a change in capacitance rather than an exact capacitance value allows for minimal circuit complexity. An electric field is used to detect a change in capacitance, as opposed to an electromagnetic field. Using an electric field rather than an electromagnetic field eliminates a need for receiving and transmitting electrodes. Additionally, since the proximity detector is used to detect a change in capacitance rather than for measuring a capacitance value, size and complexity of the circuitry is reduced. Furthermore, certain embodiments are not affected by temperature and humidity, since frequency variation is not a main parameter used to detect a change in capacitance. --.

Signed and Sealed this

Thirtieth Day of May, 2006

JON W. DUDAS
*Director of the United States Patent and Trademark Office*